United States Patent [19]
Kvitrud

[11] Patent Number: 4,632,672
[45] Date of Patent: Dec. 30, 1986

[54] SELF VENTING SYRINGE PLUNGER

[75] Inventor: James R. Kvitrud, White Bear Lake, Minn.

[73] Assignee: Minnesota Mining and Manufacturing Company, Saint Paul, Minn.

[21] Appl. No.: 785,071

[22] Filed: Oct. 7, 1985

[51] Int. Cl.$^4$ .............................................. A61B 5/14
[52] U.S. Cl. ...................................................... 604/222
[58] Field of Search ............... 604/218, 221, 222, 187, 604/82, 89, 90; 222/179.5

[56] References Cited

U.S. PATENT DOCUMENTS

| | | | |
|---|---|---|---|
| 3,331,538 | 7/1967 | Higgins | 604/222 X |
| 3,566,859 | 3/1971 | Schwartz | 604/222 X |
| 3,674,181 | 7/1972 | Marks et al. | 222/179.5 |
| 4,340,067 | 7/1982 | Rattenborg | 128/763 |
| 4,405,249 | 9/1983 | Scales | 401/182 |
| 4,492,576 | 1/1985 | Dragan | 433/90 |

*Primary Examiner*—John D. Yasko
*Attorney, Agent, or Firm*—Donald M. Sell; James A. Smith; William L. Huebsch

[57] ABSTRACT

A syringe having a barrel adapted to receive a plunger with a through passageway from the bottom wall of a groove in which an O-ring seal is positioned to the rear surface of the plunger. Upon insertion of the plunger into the barrel, the O-ring will move to a position adjacent a rear wall defining the groove over the passageway and allow air to escape from within the barrel through the passageway. When the pressure used to seat the plunger against material within the barrel is removed, the plunger will rebound slightly causing the plunger to move relative to the O-ring so that the O-ring makes an air tight seal between the plunger and the barrel. When pressure is again applied to the plunger to press the material out of the barrel, the plunger will again move relative to the O-ring to again position the O-ring over the passageway, however, the O-ring will seal the passageway sufficiently to restrict escape of a significant amount of the viscous material through the passageway.

4 Claims, 4 Drawing Figures 4,632,672

SELF VENTING SYRINGE PLUNGER

TECHNICAL FIELD

This invention relates to plungers for syringes that can vent air from between the plungers and materials in the barrels of the syringes into which the plungers are inserted.

BACKGROUND ART

Syringes typically each comprise a barrel having a through opening including a cylindrical portion; a plunger adapted to be inserted into the cylindrical portion of the opening and having a groove around its periphery; and a resiliently elastic O-ring within the groove around the plunger, which O-ring has a circular cross section with a predetermined diameter adapted to be compressed between the plunger and the cylindrical inner surface of the syringe to provide a seal therebetween.

A problem exists in removing air from between the plunger and material (e.g., a liquid or paste) within the opening in the barrel when the syringe is assembled such as at a factory or by a user of the syringe. Various plunger structures have been suggested to vent this air when the plunger is inserted (see U.S. Pat. Nos. 3,674,181; 4,340,067 and 4,405,249). These structures, however, are not useful for many materials so that some persons filling syringes have resorted to filling them under vacuum conditions, which is both expensive and time consuming.

DISCLOSURE OF THE INVENTION

The present invention provides a simple self venting plunger structure that allows plungers to be inserted into openings in barrels of syringes under atmospheric conditions without significantly compressing air between the plunger and a material in the barrel, thereby greatly facilitating the filling of syringes either in factories or elsewhere.

According to the present invention, there is provided a syringe of the type described above comprising a barrel having front and rear ends, and a through opening including a cylindrical portion defined by a cylindrical inner surface opening through the rear end of the barrel; a plunger adapted to be inserted in the cylindrical portion having front and rear surfaces, and a groove around its periphery defined by spaced front and rear generally radially extending walls of the plunger and a cylindrical bottom wall of the plunger extending between the front and rear walls; and a resiliently elastic O-ring within the groove around the plunger, which O-ring has a circular cross section with a predetermined diameter adapted to be compressed between the bottom wall of the plunger and the cylindrical inner surface of the syringe. Typically the front and rear walls defining the groove in such plungers are spaced at a distance exceeding the predetermined diameter of the O-ring to afford sliding relative movement between the O-ring and the bottom wall to move the front wall or the rear wall adjacent the O-ring.

In the improved dispenser according to the present invention the plunger has a through passageway from the bottom wall to the rear surface of the plunger, which passageway is adjacent the rear wall, has a dimension from the rear wall to the edge of the passageway farthest from the rear wall measured axially along the bottom wall that is less than the predetermined diameter of the O-ring, and is so sized that upon insertion of the plunger front surface first into the cylindrical portion the O-ring will move to a position adjacent the rear wall and allow air to escape from the through opening through the passageway to afford seating the plunger against material in the through opening. After the pressure that causes such seating is released, the plunger will rebound slightly within the barrel, causing the plunger to move relative to the O-ring to position the front wall closely adjacent the O-ring with the passageway spaced from beneath the O-ring so that the O-ring makes an air tight seal between the plunger and the barrel during storage of the filled syringe. When pressure is then applied to the plunger to press the material out of the barrel, the plunger will again move relative to the O-ring to position the rear wall against the O-ring with the O-ring over the passageway, however, because of the much higher viscosity of the material in the barrel compared to the viscosity of air, the O-ring will sufficiently seal the passageway to restrict escape of a significant amount of the material through the passageway.

It is desirable to maximize the dimension from the rear wall to the edge of the passageway farthest from the rear wall to facilitate the escape of air through the passageway as the plunger is pushed into the barrel. That dimension, however, must not be so great that a significant amount of the material to be dispensed will escape through the passageway when pressure is applied to the plunger to dispense the material. For the same size barrel, plunger, groove and O-ring, the maximum usable such dimension between the passageway and rear wall has been found to vary with the viscosity of the material to be dispensed, with a greater dimension being acceptable for higher viscosity materials.

For any such dimension between the passageway and the rear wall, the rate at which air can escape from between the material and the plunger can be increased by increasing the circumferential dimension of each passageway, or by increasing the number of passageways.

BRIEF DESCRIPTION OF THE DRAWING

The present invention will be further described with reference to the accompany drawing where like numbers refer to like parts in the several views, and wherein.

DETAILED DESCRIPTION

Figures 1, 2, 3, 4:
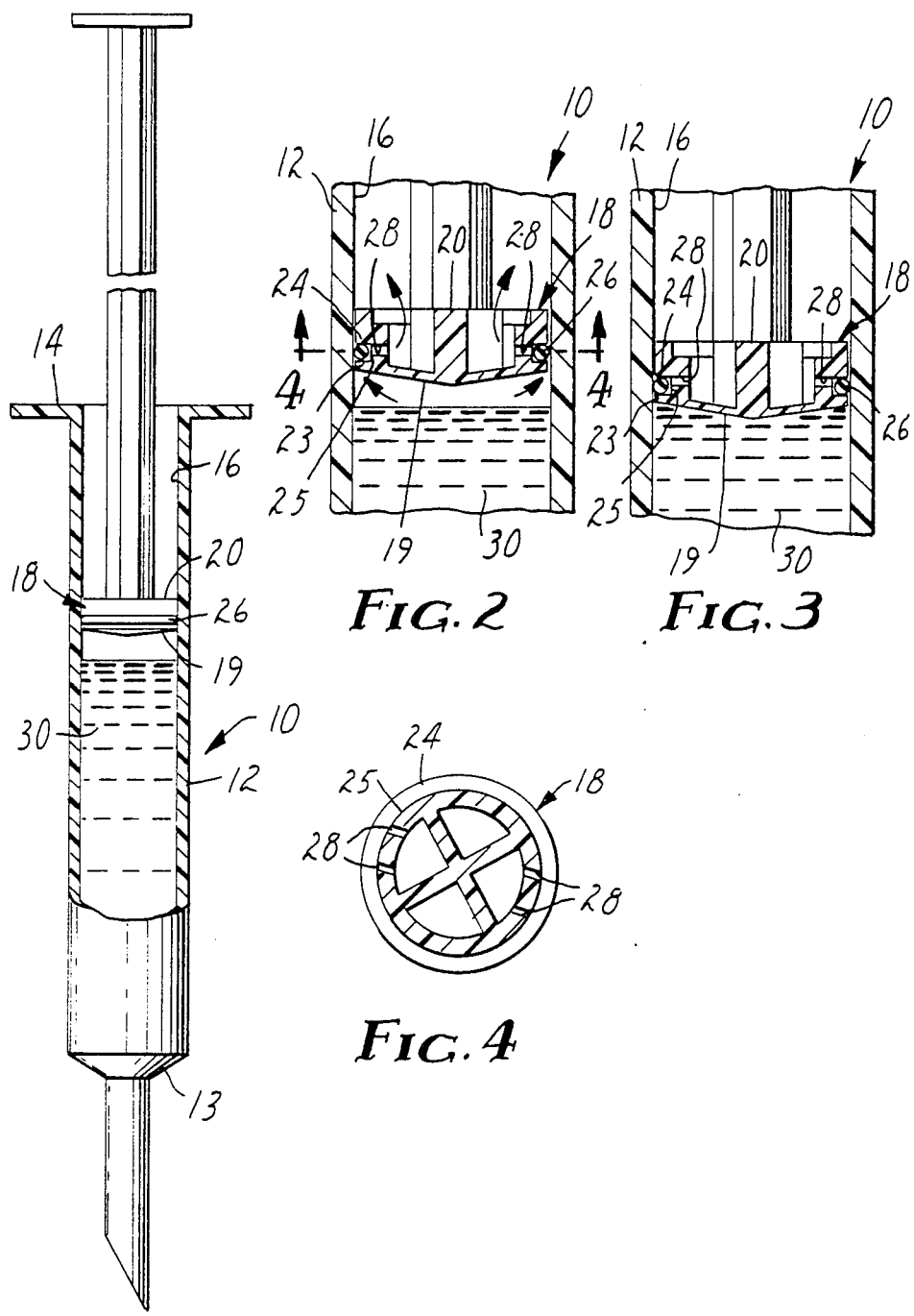
FIG. 1 is a fragmentary plan view, partially in section, of a syringe according to the present invention as a plunger is pressed into a barrel of the syringe.
FIG. 2 is an enlarged fragmentary sectional view of the plunger in the syringe of FIG. 1.
FIG. 3 is an enlarged fragmentary sectional view showing the plunger in the syringe of FIG. 1 after it has been moved into contact with material within the syringe.
FIG. 4 is a sectional view taken approximately along line 4—4 of FIG. 2.

Referring now to the drawing, there is shown a syringe according to the present invention generally designated by the reference numeral 10.

Like prior art syringes, the syringe 10 comprises a barrel 12 having front and rear ends 13 and 14, and a through opening including a cylindrical portion defined by a cylindrical inner surface 16 opening through the rear end 14 of the barrel 12; a plunger 18 adapted to be inserted into the cylindrical portion of the opening having front and rear surfaces 19 and 20, and a groove around its periphery defined by spaced front and rear generally radially extending walls 23 and 24 of the plunger 18 and a cylindrical bottom wall 25 of the plunger 18 extending between the front and rear walls 23 and 24; and a resiliently elastic O-ring 26 within the groove around the plunger 18, which O-ring 26 has a circular cross section with a predetermined diameter adapted to be compressed between the bottom wall 25 of the plunger 18 and the cylindrical inner surface 16 of the barrel 12, with the front and rear walls 23 and 24 defining the groove spaced at a distance exceeding the predetermined cross sectional diameter of the O-ring 26 to afford sliding relative movement between the O-ring 26 and the bottom wall 25 to move the front wall 23 or the rear wall 24 adjacent the O-ring 26.

The syringe 10 according to the present invention is improved in that the plunger 18 has a plurality of (i.e., four) through passageways 28 from the bottom wall 25 to the rear surface 20 of the plunger 18. The passageways 28 each are adjacent the rear wall 24, have one side generally aligned with the rear wall 24, and have a dimension from the rear wall 24 to the edge of the passageway 28 farthest from the rear wall 24 measured axially along the bottom wall 25 that is less than the predetermined cross sectional diameter of the O-ring 26, and are so selected that (1) upon insertion of the plunger 18 front surface 19 first into the cylindrical portion of the through opening, the O-ring 26 will move to a position adjacent or abutting the rear wall 24 and allow air to escape from the through opening through the passageway 28 to afford seating the front surface 19 of the plunger 18 against material 30 in the through opening intended to be dispensed from the syringe 10; (2) when the pressure that caused such seating is released, the plunger 18 will rebound slightly within the barrel 12, thereby causing the plunger 18 to move relative to the O-ring 26 to position the front wall 23 closely adjacent the O-ring 26 with the passageway 28 spaced from beneath the O-ring 26 so that the O-ring 26 makes an air tight seal between the plunger 18 and the barrel 12; and (3) when pressure is again applied to the plunger 18 to press the material 30 out of the barrel 12, the plunger 18 will again move relative to the O-ring 26 to position the rear wall 24 against the O-ring 26 with the O-ring 26 over the passageway 28, however, the O-ring 26 will sufficiently seal the passageway 28 to restrict escape of a significant amount of the material 30 through the passageway 28.

As one example, when an 0.48 centimeter (3/16 inch) inside diameter 70 durometer silicone rubber O-ring 26 having a cross sectional diameter of 0.16 centimeter (1/16 inch) is used in a groove in a polypropylene plunger 18, which groove has a 0.5 centimeter (0.200 inch) diameter cylindrical bottom wall 25 with an axial length of 0.239 centimeter (0.094 inch) between front and rear walls 23 and 24 defining the groove, a circular passageway 28 having one edge aligned with the rear wall 24 that is about 0.15 centimeter (0.060 inch) in diameter (about 85% of the cross sectional diameter of the O-ring 26) has been found to permit escape of air when the plunger 18 is inserted in a cylindrical polypropylene inner surface 0.795 centimeter (0.313 inch) in diameter while resticting escape of a paste-like material (e.g., the dental restorative sold under the trademark "SILUX" ® sold by Minnesota Mining and Manufacturing Company) when normal pressure is applied to the plunger 18 to dispense the material.

As a second example, when a 1.59 centimeter (⅝ inch) inside diameter 50 durometer silicone rubber O-ring 26 having a cross sectional diameter of 0.16 centimeter (1/16 inch) is used in a groove in a polypropylene plunger 18, which groove has a 1.63 centimeter (0.643 inch) diameter cylindrical bottom wall 25 with an axial length of 0.239 centimeter (0.094 inch) between front and rear walls 23 and 24 defining the groove, a circular passageway that is about 0.117 centimeter (0.046 inch) in diameter (about 65% of the cross sectional area of the O-ring 26) has been found to also permit escape of air when the plunger 18 is inserted in a cylindrical polypropylene inner surface 1.93 centimeter (0.76 inch) in diameter, while restricting the escape of honey-like materials of about 60,000 to 100,000 centipoise viscosity (e.g., vinyl polysiloxane impression materials sold under the trademark "EXPRESS" by Minnesota Mining and Manufacturing Company) when normal pressure is applied to the plunger 18 to dispense those materials.

The present invention has now been described with reference to one embodiment thereof. It will be apparent to those skilled in the art that many changes can be made in the embodiment described without departing from the scope of the present invention. Thus the scope of the present invention should not be limited to the structures described in this application, but only by structures described by the language of the claims and the equivalents of those structures.

I claim:

1. In a syringe comprising a barrel having front and rear ends, and a through opening including a cylindrical portion defined by a cylindrical inner surface opening through the rear end of the barrel; a plunger adapted to be inserted in said cylindrical portion having front and rear surfaces, and a groove around its periphery defined by spaced front and rear generally radially extending walls of the plunger and a cylindrical bottom wall of the plunger extending between the front and rear walls; and a resiliently elastic O-ring within the groove around the plunger, said O-ring having a circular cross section with a predetermined diameter adapted to be compressed between the bottom wall of the plunger and the cylindrical inner surface of the syringe, with the front and rear walls defining the groove spaced at a distance exceeding said predetermined diameter to afford sliding relative movement between said O-ring and said bottom wall to move said front wall or said rear wall adjacent the O-ring, the improvement wherein:

said plunger has a through passageway from said bottom wall to the rear surface of said plunger, said passageway being adjacent said rear wall, having a dimension from said rear wall to the edge of said passageway farthest from said rear wall measured axially along said bottom wall that is less than said predetermined diameter of said O-ring, and being so sized that (1) upon insertion of said plunger front surface first into said cylindrical portion, said O-ring will move to a position adjacent said rear wall and allow air to escape from said through opening through said passageway to afford seating said plunger against material in said through opening; (2) when the pressure that caused such seating of the plunger is released, the plunger will rebound slightly within the barrel, causing the plunger to move relative to said O-ring to position said front wall closely adjacent the O-ring with the passageway spaced from beneath the O-ring so that the O-ring makes an air tight seal between the plunger and the barrel; and (3) when pressure is again applied to the plunger to press the material out of the barrel, the plunger will again move relative to the O-ring to position said rear wall against the O-ring with the O-ring over the passageway, however, the O-ring will sufficiantly seal the passageway to restrict escape of a significant amount of the material through the passageway.

2. A syringe according to claim 1 wherein said dimension from said rear wall to the edge of said passageway farthest from said rear wall is less than about 85 percent of the cross sectional diameter of said O-ring.

3. A syringe according to claim 1 wherein said dimension from said rear wall to the edge of said passageway from said rear wall is about 65 percent of the cross sectional diameter of said O-ring.

4. A syringe according to claim 1 wherein said plunger has a plurality of said through passageways.

* * * * *